| United States Patent [19] | [11] Patent Number: 5,015,783 |
|---|---|
| Vora et al. | [45] Date of Patent: May 14, 1991 |

[54] PRODUCTION OF ETHERS BY THE REACTION OF ALCOHOLS AND OLEFINS

[75] Inventors: Bipin V. Vora, Darien; Peter R. Pujado, Palatine; Charles P. Luebke, Mount Prospect, all of Ill.

[73] Assignee: UOP, Des Plaines, Ill.

[21] Appl. No.: 445,255

[22] Filed: Dec. 4, 1989

[51] Int. Cl.$^5$ .............................................. C07C 41/06
[52] U.S. Cl. .................................................. 568/697
[58] Field of Search ........................................ 568/697

[56] References Cited

U.S. PATENT DOCUMENTS

| 2,720,547 | 10/1955 | Wolff et al. | 260/614 |
|---|---|---|---|
| 3,726,942 | 4/1973 | Louder | 260/683.61 |
| 4,207,076 | 6/1980 | Bove et al. | 44/56 |
| 4,219,678 | 8/1980 | Obenaus et al. | 568/697 |
| 4,302,298 | 11/1981 | Mikitenko et al. | 203/75 |
| 4,322,565 | 3/1982 | Dotson, Jr. et al. | 568/697 |
| 4,334,890 | 6/1982 | Kochar et al. | 568/697 |
| 4,334,964 | 6/1982 | Prezelj et al. | 203/14 |
| 4,371,718 | 2/1983 | Hutson, Jr. | 568/697 |
| 4,440,963 | 4/1984 | Childs | 568/697 |
| 4,490,563 | 12/1984 | Pool et al. | 568/697 |
| 4,906,787 | 3/1990 | Huang et al. | 538/697 |

FOREIGN PATENT DOCUMENTS

| 2706879 | 8/1977 | Fed. Rep. of Germany | 568/697 |
|---|---|---|---|
| 2187741 | 9/1987 | United Kingdom | 568/697 |

OTHER PUBLICATIONS

Stinson, New Plants, Processes Set for Octane Booster, Chemical & Engineering News, Jun. 25, 1979, pp. 35–36.
F. Obenaus et al., Huls-Process:Methyl Tertiary Butylether presented at the American Institute of Chemical Engineers 85th National Meeting on Jun. 4–8, 1978.
Getting the Lead Out With Ethyl T-Butyl Ether, CHEMTECH Feb. 1988, pp. 120–122.
Berbonic, ETBE: Ethanol's Motor Fuel Hope? Chemical Business, Oct. 1988, pp. 38–39.
Huels/Uop Technology for ETBE/MTBE Production by Nerlich et al., Presented at the DeWitt Petrochemical Review Houston, Tex. Mar. 28–30, 1989.
Muddarris et al., Now, MTBE from Butane, Hydrocarbon Processing, Oct. 1980, pp. 91–95.

*Primary Examiner*—Howard T. Mars
*Attorney, Agent, or Firm*—Thomas K. McBride; John G. Tolomei

[57] ABSTRACT

Processes for the production of ethers from alcohols and isoolefins are disclosed. Isoolefins having four to five carbon atoms per molecule are combined with a monohydroxy alcohol having from one to five carbon atoms per molecule and with a recycle stream comprising alcohol and water to form an etherification zone feed stream which is passed through an etherification zone to produce the desired ether. The effluent from the etherification zone is separated into an ether product and an aqueous product containing unreacted alcohol which is recycled to provide a portion of the etherification zone feed stream. Distillation can be employed to separate the effluent from the etherification zone into a bottoms product stream, comprising the ether, a distillate product comprising other hydrocarbons and the above-mentioned recycle stream. When producing ethyl-tertiary-butyl ether (ETBE), azeotropic grade ethanol, i.e., about 5 vol. % water, is preferably utilized. The utilization of the alcohol/water recycle stream can obviate the need for additional alcohol recovery from the distillate product.

11 Claims, 1 Drawing Sheet

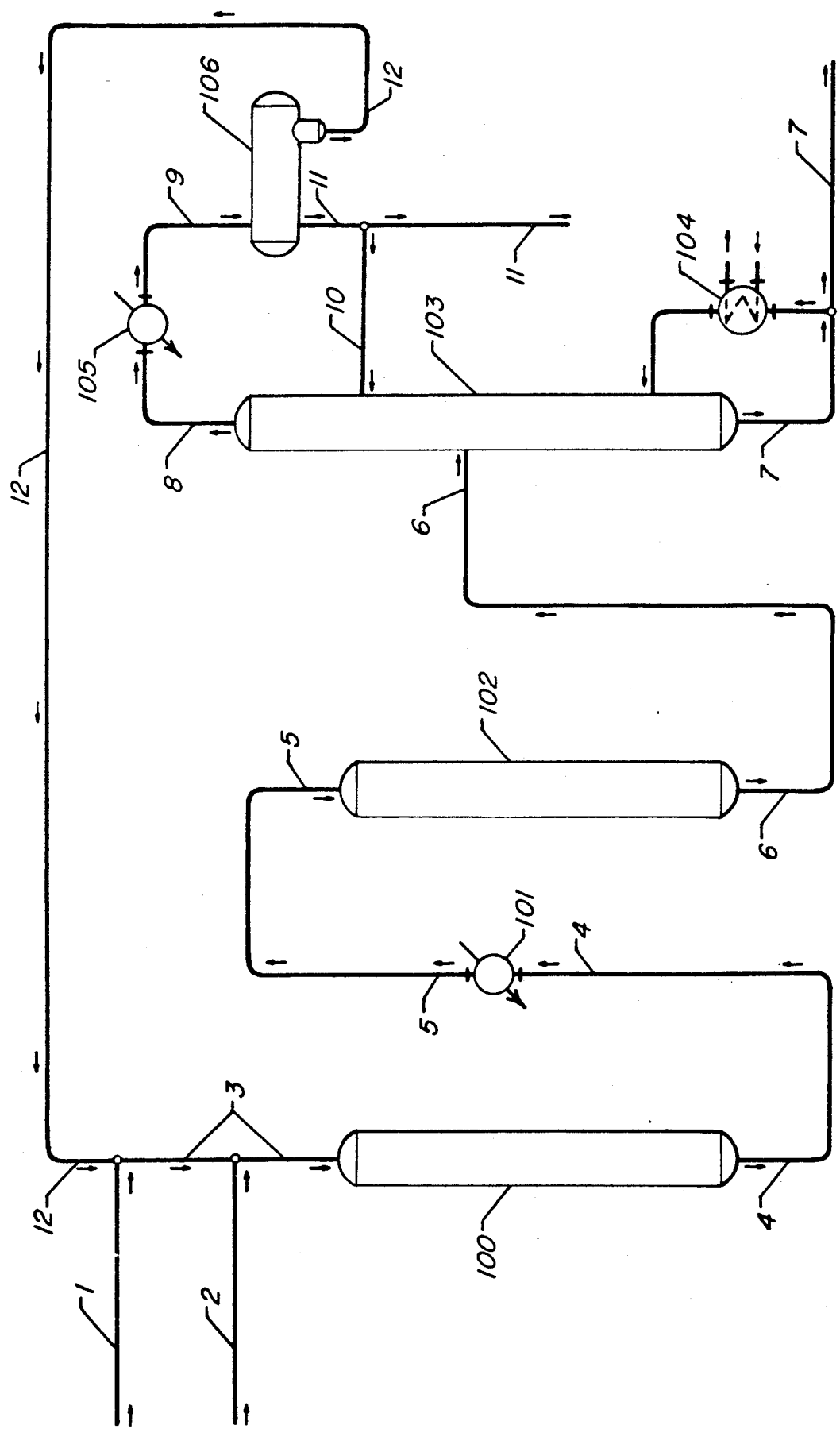

PRODUCTION OF ETHERS BY THE REACTION OF ALCOHOLS AND OLEFINS

FIELD OF THE INVENTION

The present invention generally relates to the production of ethers by the reaction of alcohols and olefins. More specifically, the present invention provides a process for the production of ethers by the reaction of monohydroxy alcohols and isoolefins in the presence of water. In one aspect of the invention, ethyl-tertiary-butyl ether is produced by the reaction of isobutene and ethanol.

BACKGROUND OF THE INVENTION

The production of ethers by the reaction of an isoolefin with an alcohol is well known and is practiced commercially. This highly selective reaction is also used to remove isoolefins, especially isobutylene, from mixed hydrocarbon streams such as the $C_4$ streams produced in an ethylene-producing steam cracking plant or in an FCC unit. Much attention has been focused on ether production due to the rapidly increasing demand for lead-free octane boosters for gasoline such as methyl-tertiary-butyl ether (MTBE).

A detailed description of processes, including catalysts, processing conditions and product recovery, for the production of MTBE from isobutylene and methanol are provided in U.S. Pat. Nos. 2,720,547 and 4,219,678 and in the following article; Stinson, *New Plants, Processes Set for Octane Booster*, CHEMICAL AND ENGINEERING NEWS, June 25, 1979 at pp. 35-36. The preferred etherification zone is described in a paper presented at the American Institute of Chemical Engineers 85th National meeting on June 4-8, 1978 by F. Obenaus et al., entitled *Huls-Process: Methyl Tertiary Butylether*.

More recently, there has been an increased commercial interest in the use of ethyl-tertiary-butyl ether (ETBE) as a lead-free octane booster for gasoline. Note, for example, the following publications: Iborra et al., *Getting The Lead Out With Ethyl t-Butyl Ether*, CHEMTECH, Feb. 1988, pp. 120-122; and Berbonic, *ETBE: Ethanol's Motor Fuel Hope?*, CHEMICAL BUSINESS, Oct. 1988, at pp. 38-39, and the paper presented at the DeWitt Petrochemical Review, Houston, Tex. Mar. 28-30, 1989 by Nierlich et al., entitled *Huels/UOP Technology for ETBE/MTBE Production*.

Ethyl-tertiary-butyl ether has long been recognized as a suitable blending cosolvent for hydrous ethanol in gasoline stocks. See U.S. Pat. No. 4,207,076. ETBE can be blended into a fuel gasoline at about a 10 to 20 volume percent level, more usually about 9 to 12%, in which the fuel comprises about 70 to 84% gasoline and 5 to 20% of 95% ethanol, i.e., grain alcohol. ETBE solubilizes grain alcohol in gasoline in all proportions thereby allowing a wide latitude in the precise amount of ethanol which can be blended with the gasoline. In addition, the presence of ETBE in the blend considerably increases its octane rating, both motor and research.

ETBE and MTBE are produced by reacting isobutene with either ethanol or methanol, resulting respectively in the formation of ETBE or MTBE. The reaction normally is conducted in liquid phase with relatively mild conditions. While mixed butene streams can be employed, only the tertiary olefin, isobutene, reacts as the conditions employed. The isobutene can be obtained from various sources, such as naphta cracking, catalytic cracking, etc. For example, refer to, Muddarris et al., *Now, MTBE from Butane*, HYDROCARBON PROCESSING, Oct. 1980, at pp. 91-95. This highly selective reaction can also be used to remove isobutene from mixed hydrocarbon streams such as the $C_4$ streams produced in steam cracking plants which produce ethylene.

The resulting reaction product stream contains the desired MTBE or ETBE, as well as unreacted isobutene and other $C_4$ hydrocarbons and methanol or ethanol. A problem that persists has been the separation of the unreacted alcohol from the ETBE or MTBE product. At equilibrium conversion, considerable alcohol remains in the reactor effluent, is difficult to remove by simple distillation, and may form troublesome azeotropes with ETBE and MTBE.

Several solutions to this problem have been disclosed. For example, U.S. Pat. No. 3,726,942 discloses the removal of methanol from the unreacted hydrocarbons withdrawn from an MTBE reaction zone through the use of molecular sieves. U.S. Pat. No. 4,322,565 discloses the removal of alcohols from the effluent of an etherification reaction zone through absorption of the alcohol on solid calcium chloride. The reference also discloses that the absorbent can be regenerated with a hot hydrocarbon stream which can be charged to the etherification reactor to recycle the alcohol. This absorption step is a bulk removal which replaces fractional distillation of the etherification reaction zone effluent.

U.S. Pat. No. 4,371,718 discloses that the effluent of the MTBE reactor may be fractionated to yield a $C_4$ stream which is then passed through methanol adsorption zones. The adsorption zones are regenerated with hot hydrocarbons which are then passed into the MTBE reactor. The methanol-free $C_4$ stream is then passed into an alkylation zone.

U.S. Pat. No. 4,440,963 discloses a process wherein the fractionation of the methanol- or ethanol-containing methyl-(or ethyl)-tertiary-butyl ether reactor effluent is improved by employing 2-methylpentane to azeotrope methanol or ethanol overhead, or by using 1,1,3-trichloro-1,2,2-trifluoroethane (F113) to azeotrope methanol overhead, leaving a substantially pure MTBE or ETBE bottoms.

U.S. Pat. No. 4,490,563 discloses a process wherein MTBE is recovered from an ether-containing effluent by fractionation. In one aspect of the process of the above-described patent, when driers are not used to pretreat the hydrocarbon feed to MTBE manufacture, i.e., water-containing feeds, a separate water-methanol phase occurs in the fractionation overhead which is separately processed in a methanol fractionator and the water recovered is used to water wash the separated hydrocarbon phase from the overhead while methanol is recycled to MTBE manufacture.

U.S. Pat. No. 4,302,298 discloses a process for isolating methyl tert-butyl ether contained in the reaction product of methanol with a $C_4$ hydrocarbon cut containing isobutene, comprising fractionating said reaction product by introducing it at an intermediate point of a distillation zone, recovering methyl tert-butyl ether at the bottom thereof and, at the top thereof, a mixture of $C_4$ hydrocarbons with methanol. The $C_4$ hydrocarbons mixture is washed with water to form a water-methanol fraction and a $C_4$ hydrocarbon fraction, a portion of which is fed back as reflux to the top of the distillation zone and another portion discharged. The remaining water-methanol mixture is fractionated by distillation.

U.S. Pat. No. 4,334,964 discloses a method for separating mixture of reaction products produced in the catalytic etherification of a lower isoolefin with methanol which comprises adding water to said reaction product to form a hydrocarbon phase containing the product ether and an aqueous phase containing methanol and a tertiary alcohol. The products are thereafter separated by distillation and the methanol is recycled to the reaction feed stream.

The processes described above provide, by methods including distillation, absorption and adsorption, for the recovery and recycle of the monohydroxy alcohols, e.g., methanol and ethanol, to the etherification reactor feed. These separation steps are effective to avoid alcohol losses with the product streams. However, some separation steps, particularly those which provide for the recovery of the monohydroxy alcohols from the azeotropic mixtures of unreacted alcohols and hydrocarbons, can unduly increase the overall process complexity. Accordingly, processes for the etherification of monohydroxy alcohols and isoolefins are sought which can provide for the recovery and recycle of unreacted alcohols without complicated separation steps. Such processes are especially desired in the production of ETBE wherein the azeotropic ethanol content with hydrocarbons is typically lower than the corresponding azeotropic methanol content in MTBE production. Moreover, since ethanol is often obtainable in azeotropic form, i.e., about 5 vol. % water, processes are sought for the production of ETBE which can utilize azeotropic ethanol as a feed source.

SUMMARY OF THE INVENTION

The present invention provides processes for the production of ethers by the reaction of alcohols and isoolefins. By performing the etherification reaction in the presence of water and having water present in the effluent stream from the reaction zone, i.e., etherification zone effluent stream, it is now possible to conveniently recover the unreacted alcohols in an aqueous phase from the etherification zone effluent stream. The unreacted alcohols are recycled, along with water contained in the aqueous phase to the etherification zone. In the aspect of the invention wherein ETBE is produced, azeotropic ethanol can be used to provide water in the reactor feed.

Accordingly, in a broad aspect of the present invention, there is provided a process for producing ethers which include the steps of: (a) passing a feed stream comprising isoolefins having four to five carbon atoms, at least one monohydroxy alcohol having from one to five carbon atoms and water, wherein the water comprises at least about 0.1 vol. % of the feed stream, to an etherification zone, at etherification conditions and withdrawing an etherification zone effluent from the etherification zone containing at least one ether, at least one alcohol and water; (b) separating the etherification zone effluent into a first product stream containing ether, and a second product stream containing alcohol and water; and (c) recycling at least a portion of the second product stream to the etherification zone to comprise a portion of the feed stream.

In a narrower aspect of the present invention, there is provided a process for producing ethers which includes the steps of: (a) passing a feed stream containing isoolefins and other hydrocarbons having four to five carbon atoms, at least one monohydroxy alcohol having from one to about five carbon atoms and water to an etherification zone at etherification conditions to provide an etherification zone effluent stream containing ether, alcohol, other hydrocarbons, and water; (b) passing the etherification zone effluent stream to a distillation column at distillation conditions to provide a bottoms product stream containing ether and an overhead stream containing alcohol, other hydrocarbons and water; (c) cooling the overhead stream to form a liquid hydrocarbon phase and a liquid aqueous phase containing alcohol and water; (d) refluxing the distillation column with a portion of the hydrocarbon phase and recovering the remaining portion as a distillate product stream; and (e) providing a recycle stream containing the aqueous phase and passing at least a portion thereof to the etherification zone to comprise a portion of the feed stream.

In still yet another specific aspect of the present invention there is provided a process for producing ethyl-tertiary-butyl ether which includes the steps of: (a) passing a feed stream containing isobutene, ethanol, other $C_4$ hydrocarbons and water to an etherification zone at etherification conditions to provide an etherification zone effluent stream containing ethyl-tertiary-butyl ether, ethanol, tertiary-butyl alcohol, other $C_4$ hydrocarbons, and water; (b) passing the etherification zone effluent stream to a distillation column at distillation conditions to provide a bottoms product stream containing said ethyl-tertiary-butyl ether and tertiary-butyl alcohol, and an overhead stream containing ethanol, water and other $C_4$ hydrocarbons; (c) cooling the overhead stream to form a liquid hydrocarbon phase and a liquid aqueous phase containing ethanol and water; (d) refluxing the distillation column with a portion of the hydrocarbon phase and recovering the remaining portion as a distillate product stream; and (e) providing a recycle stream containing the said aqueous phase and passing at least a portion thereof to the etherification zone to comprise a portion of the feed stream.

BRIEF DESCRIPITON OF THE DRAWING

The Drawing illustrates the process flow for an aspect of the invention wherein ETBE is produced by the reaction of ethanol and isobutene in the presence of water.

DETAILED DESCRIPTION OF THE INVENTION

The present invention provides processes for the conversion of isoolefins and monohydroxy alcohols in an etherification zone to form ethers which are suitable for use as blending components in gasoline. In accordance with the present invention, the reaction may be used to convert isoolefins having from four to five carbon atoms per molecule, preferably isobutene, and monohydroxy alcohols having from one to about five carbon atoms, preferably methanol, and more preferably ethanol. When an ethanol stream is used as the alcohol, it may contain water since the etherification reaction of the present invention is conducted in the presence of water as hereinafter described. Accordingly, in a preferred aspect of the present invention azeotropic ethanol, i.e., containing about 5 vol. % water, comprises the alcohol feed component. Azeotropic ethanol is readily commercially available and less expensive than pure ethanol. Hence the use of azeotropic ethanol can improve the overall process economics. The isobutene feed component can be derived from a variety of sources which are not critical to the process of the present invention. Moreover, the isobutene content of the feed is also not critical. One typical source for the isobutene feed component is a $C_4$ fraction derived from a FCC unit, i.e., fluidized catalytic cracking. Another is the $C_4$ product from a process for the catalytic dehydrogenation of LPG, i.e., liquified petroleum gas, or LNG, i.e., liquified natural gas. Still yet another source for isobutene is the $C_4$ fraction derived from a steam cracker. Such feed sources typically contain isobutene in concentrations of from about 5 to about 50 wt. % with the balance comprising other butenes and butanes. Not infrequently, other hydrocarbons having an aliphatic moiety higher and lower than $C_4$ will be present in the feed along with the $C_4$ fraction.

When the above described preferred feed reactants are used, the product slate from the process of the present invention can include, in addition to MTBE and ETBE, other ethers such as methyl tertiary-amyl ether and ethyl tertiary-amyl ether. In some instances, it may be desirable to perform the etherification as a mixed feed comprising more than one monohydroxy alcohol or more than one isobutene.

Along with the fresh feed isoolefin and alcohol components hereinbefore described, the feed stream to the etherification zone also comprises a recycle stream containing alcohol and water. The recycle stream is preferably obtained from the aqueous phase of the overhead distillate of an etherification zone effluent distillation column, which is hereinafter described in detail.

In the etherification zone, isoolefins are reacted with alcohols to form an ether compound. In the process of the present invention, water is also introduced into the etherification zone. A portion of the water in the feed to the etherification zone, typically from about 50 to about 80 wt. % at the etherification conditions employed, will react with isobutene and be converted to tertiary-butyl alcohol (TBA). While an excessive amount of TBA formation is undesirable since it can cause a suppression or reduction in the yield of the desired ether product, lesser amounts are tolerable. In fact, TBA is also suitable for blending with gasoline. In accordance with the present invention, the water content in the feed stream to the etherification zone will be at least 0.1 vol. %, and preferably at least 5 vol. % but less than 15 vol. % of the total feed stream, and more preferably less than 10 vol. % on a liquid volume basis.

According to the process of the present invention, the isobutene or other isoolefin, ethanol or other feed alcohol, and a recycle stream containing recovered excess alcohol and water are passed into the etherification zone and contacted with a suitable catalyst while maintained at etherification conditions.

A wide range of materials are known to be effective as etherification catalysts for the preferred reactants including mineral acids such as sulfuric acid, boron trifluoride, phosphoric acid on kieselguhr, phosphorus-modified zeolites, heteropoly acids, and various sulfonated resins. The use of a sulfonated solid resin catalyst is preferred. These resin type catalysts include the reaction products of phenolformaldehyde resins and sulfuric acid and sulfonated polystyrene resins including those crosslinked with divinylbenzene. Further information on suitable etherification catalysts may be obtained by reference to U.S. Pat. Nos. 2,480,940, 2,922,822, and 4,270,929 and the previously cited etherification references.

A wide range of operating conditions are employed in processes for producing ethers from olefins and alcohols. Many of these include vapor, liquid or mixed phase operations. Processes operating with vapor or mixed phase conditions may be suitably employed in this invention. The preferred etherification process uses liquid phase conditions.

The range of etherification conditions for processes operating in liquid phase includes a broad range of suitable conditions including a superatmospheric pressure sufficient to maintain the reactants as a liquid phase, generally below about 50 bars, and a temperature between about 30° C. (85° F.) and about 100° C. (212° F.). Even in the presence of additional light materials, pressures in the range of 10 to 40 bars are generally sufficient. A preferred temperature range is from 50° C. (120° F.) to 100° C. (212° F.). High conversion in a moderate volume reaction zone can, therefore, be obtained if the initial section of the reaction zone, e.g., the first two-thirds, is maintained above 70° C. (160° F.) and the remainder of the reaction zone is maintained below 50° C. (120° F.). This may be accomplished most easily with two reactors. The ratio of feed alcohol to isoolefin should normally be maintained in the broad range of 1:1 to 2:1. With the preferred reactants, good results are achieved if the ratio of ethanol to isobutene is between 1.05:1 and 1.5:1. An excess of ethanol, above that required to achieve satisfactory conversion at good selectivity, should be avoided as some decomposition of ethanol to diethylether may occur which may increase the load on separation facilities.

The effluent from the etherification zone comprises the product ether, e.g., MTBE or ETBE, unreacted monohydroxy alcohol, e.g., methanol or ethanol, other by product alcohols such as TBA when isobutene is present in the feed, hydrocarbons other than isoolefins, and water. The effluent may also contain other compounds formed in the etherification zone such as dimethyl ether (DME). The effluent from the etherification zone passes from the etherification zone to a separation section for the recovery of product.

In the separation section of the process of the present invention, distillation is employed to recover the product ethers and provide a recycle stream comprising water and alcohol and a distillate product stream, e.g., $C_4$ raffinate hydrocarbons, which is substantially free of isolefins. This separation can be performed in a single column. Depending upon the specification for the ether product, it may be suitable for use as withdrawn from the bottom of the separation column or may require additional separation to remove alcohol which may be present in the form of an azeotrope mixture of the product ether. The column will also provide an overhead stream made up of a lighter fraction that contains unreacted feed components such as isoolefins, if any, alcohol and hydrocarbons other than isoolefins, which make up in part the remainder of the etherification zone effluent. Alcohol present in the overhead stream is unreacted excess alcohol in an amount equivalent to its azeotropic composition with the hydrocarbons. Other streams such as side-draw streams may be additionally employed as required. The use of such additional streams is well known to those skilled in the art and need not be further disclosed herein.

The overhead stream from the distillation column is cooled to provide a condensate having an aqueous phase which contains water and alcohol and a hydrocarbon phase containing $C_4$ and $C_5$ hydrocarbons other than isoolefins. It is to be understood, however, that it is within the scope of the present invention for the overhead stream to contain small amounts of isoolefins. The actual amount of isoolefins present in the overhead will be dictated by the distillation parameters utilized. In accordance with the present invention, a portion of the hydrocarbon phase is used to reflux the column. The remaining portion of the hydrocarbon phase is recovered as a distillate product stream.

When ethanol is used as the reactant alcohol, some ethanol and essentially all of the $C_4$ hydrocarbons and water will be present in the overhead stream. The azeotropic concentration of ethanol in $C_4$ hydrocarbons at typical operating conditions is from about 0.2 to about 0.5 vol. %. Accordingly, a substantial portion of the overhead ethanol will be dissolved in the aqueous phase of the overhead distillate. Hence, by recycling the aqueous phase of the overhead distillate to the etherification zone, recovery of the unreacted ethanol is achieved. Moreover, the distillate product stream, e.g., $C_4$ raffinate is substantially free of alcohol and may not require further purification.

On the other hand, when methanol is used as the feed alcohol, more of it will be present in the overhead because the azeotropic concentration of methanol in $C_4$ hydrocarbons at typical operating conditions is from about 2 to about 4 vol. %. Accordingly, a relatively high fraction of the overhead methanol may be present in the hydrocarbon phase. In such instances, further alcohol recovery from distillate product may be desired.

When further alcohol recovery from the distillate product stream is desired, an alcohol recovery unit can be employed. Typical alcohol recovery units can reduce the alcohol concentration in the distillate product stream, e.g., $C_4$ raffinate, to less than 10 wt. ppm. The preferred alcohol recovery system is a water washed system that absorbs alcohol from the remaining hyrrocarbons in the reactant stream and includes a separation column for recovery of the alcohol and recycle of the water. Another type of alcohol recovery unit utilizes a solid adsorbent to preferentially adsorb the alcohol component from the hydrocarbon phase. Alcohol separated in the alcohol recovery unit is preferably recycled to the etherification zone to provide a portion of the alcohol reactant. The remainder of the distillate product stream can then be recovered for further downstream processing, e.g., alkylation.

The aqueous phase of the overhead stream contains unreacted alcohol and, as hereinbefore described, is suitable for recycling to the etherification zone. Therefore, in accordance with the present invention, at least a portion of the aqueous phase is recycled to the etherification zone to comprise a portion of the feed thereto. Recycling this stream provides a convenient method for recovering alcohol from the overhead stream. Moreover, particularly when the reactant alcohol is ethanol, recycling can obviate the need for further alcohol recovery methods. While in many instances it may be desirable to recycle the entire aqueous phase, it is believed that combining a portion of the aqueous phase with the overhead stream prior to cooling the overhead can enhance the efficiency of the ethanol recovery. Accordingly, it is preferred that any portion of the aqueous phase that is not recycled to the etherification zone be combined with the overhead, e.g., at the inlet of the overhead condenser.

The bottoms product stream from the distillation column typically contains unreacted alcohol, particularly when heavier alcohols such as ethanol are used, and tertiary-alkyl alcohols, e.g., TBA, as well as the product ethers. In some instances, the bottoms product stream will be suitable for use without further purification. In instances where other purification is required, or when it is desired to recover the alcohol contained therein, any conventional separation process such as distillation or adsorption can be employed. In the case wherein an additional distillation step is employed to purify the product stream, the additional distillation column is preferably operated to provide an overhead comprising an alcohol-ether azeotrope and a bottoms product comprising product ether. The alcohol-ether azeotrope is preferably recycled to the etherification zone. Further details of such separation processes are well known in the art and need not be further discussed herein.

This invention will be further described in the context of an example for the production of ETBE. The description of this invention in terms of this specific process example is not meant to limit this invention to the particular details disclosed herein. This example is based on engineering calculations and experience with the operation of similar process units. The drawing provides a schematic drawing for this type of operation. The drawing shows only the equipment that is useful in the description of the process. The utilization of other miscellaneous hardware such as heaters, coolers, valves, reboilers, pumps, instrumentation, and controls have been omitted as not essential to a clear understanding of the process, the use of such hardware being well within the purview of one skilled in the art.

Referring to the drawing, an FCC derived $C_4$ fraction containing isobutene is charged to the process through line 1. An ethanol free stream comprising azeotropic ethanol, i.e., about 5 vol. % water, is charged to the process through line 2. Lines 1 and 2 are combined with line 12 which contains ethanol and water, the source of which is hereinafter set forth, to provide a first reactor feed, line 3, which has a 1:1 to 1.1:1 ratio of ethanol to isobutene. The first reactor feed is passed through an etherification zone which contains two etherification reactors, 100 and 102 with cooling therebetween, i.e., water cooler 101. Both reactors contain a sulfonic resin catalyst of the type hereinbefore described and a sufficient quantity thereof to promote the desired reaction. It is to be understood that the etherification zone of the present invention can have one or more individual reactors with cooling or other process steps therebetween. The etherification zone feed is passed through the first reactor at a temperature of about 70° C. and a pressure of about 10 to 20 bars, wherein a part of the isobutene reacts. The heat of reaction is removed by cooling effluent stream 4 in water cooler 101 to maintain a temperature of about 45° C. into the second reactor, via line 5. In the second reactor, 102, the reaction of the remaining isobutene is substantially completed. Precise temperature control in the etherification zone is important because at higher temperatures, isobutene can oligomerize and ETBE formation becomes more incomplete with rising temperatures because of the noticeably reversible equilibrium reaction. At lower temperatures, the reaction rate can decrease considerably. The actual temperature to be utilized will depend on various factors such as the particular catalyst, feed components, and concentrations and reactor design.

The effluent from the second reactor is passed via line 6 to column 103 which is maintained at a temperature of from about 45° to about 80° C. and a pressure of about 5 to about 12 bar at the top thereof and at a temperature of from about 135° to about 170° C. and a pressure of from about 5 to about 12 bar at the bottom thereof. The column heat is supplied by reboiler 104. A bottoms product stream comprising ETBE, some ethanol and TBA is withdrawn from the process via line 7. An overhead stream, line 8, is cooled in condensor 105 and passed via line 9 to tank 106 wherein a hydrocarbon phase comprising primarily $C_4$ hydrocarbons other than isobutene and an aqueous phase comprising ethanol and water are formed. A portion of the hydrocarbon phase is refluxed to the distillation column at a reflux to feed ratio of about 0.4:1, line 10. The remaining portion of the hydrocarbon phase is withdrawn as a distillate product stream, i.e., $C_4$ raffinate, via line 11. The aqueous phase of the overhead distillate is withdrawn via line 12 and recycled and combined with lines 1 and 2 to comprise the feed to the zone. A portion of the aqueous phase from line 12 can optionally be combined with the overhead distillate at or near the inlet to the overhead condensor to enhance the recovery of ethanol.

The following table sets forth a material balance for the process described above with reference to the drawing.

TABLE

| Line No. | | 1 | 2 | 12 | 3 | 6 | 7 | 8 | 11 |
|---|---|---|---|---|---|---|---|---|---|
| | | | | | Etherification Zone | | ETBE | | |
| Components | MW | $C_4$ Feed lb/hr | Fresh EtOH lb/hr | Aqueous Phase Rec lb/hr | Feed lb/hr | Effluent lb/hr | Product lb/hr | Ovhd lb/hr | $C_4$Raff lb/hr |
| $H_2O$ | 18.016 | 0.00 | 64.80 | 58.76 | 123.56 | 63.04 | 0.00 | 63.04 | 4.29 |
| $=iC_4$ | 56.104 | 1500.00 | 0.00 | 0.00 | 1500.00 | 75.00 | 0.00 | 75.00 | 75.00 |
| EtOH | 46.068 | 0.00 | 1231.41 | 61.85 | 1293.26 | 289.91 | 226.33 | 63.58 | 1.73 |
| ETBE | 102.172 | 0.00 | 0.00 | 0.00 | 0.00 | 2196.59 | 2196.51 | 0.09 | 0.09 |
| TBA | 74.120 | 0.00 | 0.00 | 0.00 | 0.00 | 259.36 | 259.28 | 0.08 | 0.08 |
| DEE | 74.120 | 0.00 | 0.00 | 0.00 | 0.00 | 10.40 | 0.00 | 10.40 | 10.40 |
| DIB | 112.208 | 0.00 | 0.00 | 0.00 | 0.00 | 22.50 | 22.50 | 0.00 | 0.00 |
| $C_4$'s | 58.120 | 8500.00 | 0.00 | 0.00 | 8500.00 | 8500.00 | 2.20 | 8497.80 | 8497.80 |
| Total | | 10000.00 | 1296.21 | 120.61 | 11416.82 | 11416.82 | 2706.82 | 8710.00 | 8589.39 |
| BPSD | | 1202.6 | 110.6 | 9.4 | 1322.6 | 1295.0 | 244.4 | 1050.6 | 1041.3 |

In the table presented above, the following abbreviations are used; $H_2O$ - water, $=iC_4$ - isobutene, EtOH - ethanol, ETBE - ethyl-tertiary-butyl ether, TBA - tertiary-butyl alcohol, DEE - diethyl ether, DIB - di-isobutene, $C_4$'s - $C_4$ alkanes and olefins other than isobutene.

We claim:

1. A process for producing ethers comprising:
    (a) passing a feed stream comprising isoolefins and other hydrocarbons having four to five carbon atoms, at least one monohydroxy alcohol having from one to five carbon atoms and water to an etherification zone at etherification conditions and withdrawing an etherification zone effluent stream from said etherification zone comprising at least one ether, at least one alcohol, said other hydrocarbons, and water;
    (b) passing said etherification zone effluent stream to a distillation column at distillation conditions and separating said etherification zone effluent stream into at least a bottoms product stream comprising said at least one ether and an overhead stream comprising said at least one alcohol, said other hydrocarbons and water;
    (c) cooling said overhead stream to form a liquid hydrocarbon phase comprising said other hydrocarbons, and a liquid aqueous phase comprising said at least one alcohol and water;
    (d) refluxing the distillation column with a portion of said hydrocarbon phase and recovering the remaining portion of said hydrocarbon phase as a distillate product stream;
    (e) recycling a first portion of said aqueous phase to the etherification zone to comprise a portion of said feed stream; and
    (f) combining the remaining portion of said aqueous phase with sai overhead stream prior to said cooling thereof.

2. The process of claim 1 wherein said feed stream comprises from about 0.1 to about 15 vol. % water.

3. The process of claim 1 wherein said at least one monohydroxy alcohol in said feed is ethanol and said isoolefin is isobutene.

4. The process of claim 3 wherein said etherification zone effluent stream comprises ethyl-tertiary-butyl ether.

5. The process of claim 4 wherein said etherification zone effluent stream further comprises tertiary-butyl alcohol and ethanol.

6. The process of claim 1 wherein the etherfication zone contains a sulfonated solid resin catalyst and operates at a temperature in the range of from about 30° to about 100° C. and a pressure of from about 10 to about 40 bars.

7. A process for producing ethyl-tertiary-butyl ether comprising:
    (a) passing a feed stream comprising isobutene and other $C_4$ hydrocarbons, ethanol, and water to an etherification zone containing a sulfonated solid resin catalyst at etherification conditions and withdrawing an etherification zone effluent stream comprising ethyl-tertiary-butyl ether, ethanol, tertiary-butyl alcohol, said other $C_4$ hydrocarbons, and water;
    (b) passing said etherification zone effluent stream to a distillation zone at distillation conditions and separating said etherification zone effluent stream into at least a bottoms product stream comprising said ethyl-tertiary-butyl ether and tertiary-butyl alcohol, and an overhead stream comprising ethanol, water and said other $C_4$ hydrocarbons;
    (c) cooling said overhead stream to form a liquid hydrocarbon phas comprising said other $C_4$ hydrocarbons, and a liquid aqueous phase comprising ethanol and water;
    (d) refluxing the distillation column with a portion of said hydrocarbon phase and recovering the remaining portion of said hydrocarbon phase as a distillate product stream; and (e) recycling a first portion of said aqueous phase to the etherification zone to provide a portion of said feed stream; and (f) combining the remaining portion of said aqueous phase with said overhead stream prior to said cooling thereof.

8. The process of claim 7 wherein said first portion is from about 10 to 100% by weight of the aqueous phase.

9. The process of claim 7 wherein the distillation column is maintained at a temperature of from about 45° to about 80° C. and a pressure of from about 5 to about 12 bar at the top thereof and a temperature of from about 135° to about 170° C. and a pressure of from about 5 to about 12 bar at the bottom thereof.

10. The process of claim 7 wherein said ethanol feed contains about 5 vol. % water.

11. The process of claim 1 wherein the feed stream comprises fresh alcohol and recycle alcohol.

* * * * *